US011536827B2

(12) United States Patent
Roberts et al.

(10) Patent No.: US 11,536,827 B2
(45) Date of Patent: Dec. 27, 2022

(54) METHOD FOR ASSESSING THE AMOUNT OF ROLLING REQUIRED TO ACHIEVE OPTIMAL COMPACTION OF PRE-ROLLED ASPHALT PAVEMENT

(71) Applicants: Roger Roberts, Amesbury, NH (US); David Cist, Winchester, MA (US)

(72) Inventors: Roger Roberts, Amesbury, NH (US); David Cist, Winchester, MA (US)

(73) Assignee: Geophysical Survey Systems, Inc., Nashua, NH (US)

( * ) Notice: Subject to any disclaimer, the term of this patent is extended or adjusted under 35 U.S.C. 154(b) by 475 days.

(21) Appl. No.: 16/785,768

(22) Filed: Feb. 10, 2020

(65) Prior Publication Data
US 2020/0256976 A1    Aug. 13, 2020

Related U.S. Application Data

(60) Provisional application No. 62/802,797, filed on Feb. 8, 2019.

(51) Int. Cl.
| | | |
|---|---|---|
| *G01S 13/88* | (2006.01) | |
| *G01N 33/42* | (2006.01) | |
| *G01S 13/86* | (2006.01) | |
| *E01C 19/18* | (2006.01) | |
| *E01C 19/28* | (2006.01) | |

(52) U.S. Cl.
CPC .......... *G01S 13/885* (2013.01); *G01N 33/42* (2013.01); *G01S 13/86* (2013.01); *G01S 13/865* (2013.01); *E01C 19/18* (2013.01); *E01C 19/288* (2013.01)

(58) Field of Classification Search
None
See application file for complete search history.

(56) References Cited

U.S. PATENT DOCUMENTS 4,698,634 A * 10/1987 Alongi ............... G01S 13/0209
                                                    342/159
5,835,053 A * 11/1998 Davis ................ G01S 13/0209
                                                    342/22

(Continued)

FOREIGN PATENT DOCUMENTS

CN        106940370 A  *  7/2017  ........... G01S 13/885

*Primary Examiner* — Bernarr E Gregory
(74) *Attorney, Agent, or Firm* — Michael J. Feigin, Esq.; Feigin and Fridman LLC (57) ABSTRACT

A ground penetrating radar device and/or other sensor such as LIDAR, pressure, or temperature sensors is mounted on a mobile device, and is adapted, during motion of the mobile device, to sense characteristics of asphalt pavement on which the mobile device is moving, prior to compaction of the asphalt pavement by rollers. A processor, functionally associated with at least one sensor, receives from the sensor signals relating to characteristics of the asphalt pavement on which the mobile device is moving, and computes, based on the received signals, at least one compaction characteristic of the asphalt pavement. The processor provides a mapping of computed desired change in compaction characteristics to regions of the asphalt pavement during the rolling process. During rolling, at least one sensor measures the change in compaction and assesses when the change in compaction matches the desired optimal compaction based on the pre-generated map.

16 Claims, 8 Drawing Sheets

(56) References Cited

U.S. PATENT DOCUMENTS

| | | | | |
|---|---|---|---|---|
| 7,226,239 | B2* | 6/2007 | Stridiron | E01C 19/288 404/84.1 |
| 7,591,608 | B2* | 9/2009 | Hall | E01C 19/288 404/133.05 |
| 7,731,450 | B2* | 6/2010 | Congdon | E01C 19/288 701/50 |
| 8,635,903 | B2* | 1/2014 | Oetken | E01C 19/288 73/78 |
| 9,068,295 | B2* | 6/2015 | Rutz | E01C 19/48 |
| 9,290,894 | B2* | 3/2016 | Eul | E01C 19/48 |
| 10,227,738 | B2* | 3/2019 | Horn | E01C 23/01 |
| 10,494,774 | B2* | 12/2019 | Roberts | E01C 19/288 |
| 10,920,381 | B2* | 2/2021 | Marsolek | E01C 19/288 |
| 2002/0190728 | A1* | 12/2002 | Gandrud | G01N 33/42 324/663 |
| 2005/0078028 | A1* | 4/2005 | Cist | G01V 3/12 342/179 |
| 2005/0150278 | A1* | 7/2005 | Troxler | G01N 33/42 73/78 |
| 2015/0268218 | A1* | 9/2015 | Troxler | G01S 13/885 342/21 |

\* cited by examiner

METHOD FOR ASSESSING THE AMOUNT OF ROLLING REQUIRED TO ACHIEVE OPTIMAL COMPACTION OF PRE-ROLLED ASPHALT PAVEMENT

FIELD OF THE DISCLOSED TECHNOLOGY

The disclosed technology relates generally to compaction of asphalt concrete, and, more specifically, to a method to calculate a desired amount of compaction of asphalt concrete at specific locations, at the time of initial compaction by a paving machine, prior to final compaction by rollers.

BACKGROUND OF THE DISCLOSED TECHNOLOGY

Improperly compacted asphalt is a well-known cause of pre-mature road failure, which is typically evidenced by occurrences such as cracking, stripping, and pot-holes. Various methods are employed to assess the degree of compaction of newly paved roads for quality assurance purposes, to avoid such improper compaction of asphalt. Such methods include use of nuclear gauge, non-nuclear gauge, coring, and ground penetrating radar (GPR). Of the above listed methods, GPR is the one technique that can feasibly provide a spatial map of compaction levels across and along the newly paved road. The benefit of full coverage, as opposed to random sampling of the compaction levels, cannot be understated. Fully covered measurement of compaction levels permits collaboration of the contractor with the road owner to accurately assess the quality of work. It also can be used to fine-tune contractor paving practices in future paving jobs. Furthermore, a better road means cost savings to the road owner and also potentially greater profit for the contractor as better practices may lead to better compaction and hence contract bonuses depending on how the paving job contract is structured. Additionally, higher quality work by the contractor may lead to more paving jobs.

The current practice, when using GPR, is to calculate the dielectric of the asphalt after it has been compacted using rollers. The dielectric of a particular asphalt mix, which contains mostly aggregate, bitumen, and air, varies depending on the percentage of air in the mix, which, in turn, is related to the degree of compaction. Dielectric measurements are typically performed on samples of an asphalt mix possessing a range of compaction levels to generate a curve relating compaction to dielectric for a particular asphalt mix.

Certain assumptions are commonly made involving the use of dielectrics obtained from GPR for assessment of asphalt compaction. The main assumption is that the dielectric properties and the proportions of the solid and liquid asphalt constituents (i.e. aggregate and bitumen) are invariant for a particular asphalt mix during the course of a paving job. Many studies have shown this assumption to be generally valid. However, there are occurrences where samples of asphalt, typically obtained by coring, possess dielectrics and a compaction level that do not match the dielectric versus compaction curve previously generated for a particular asphalt mix.

For example, the dielectric of the aggregate may change slightly when newly constructed asphalt pavements contain recycled asphalt pavement (RAP). The dielectric properties of the RAP vary due to changes in RAP's aggregate, which depend on the types and percentages of minerals in the aggregate particles. These mineral dielectrics may range from 3 to 10 and higher. A change of as little as 0.5 in dielectric of an asphalt mix may mean the difference between properly and improperly compacted asphalt. Considering that up to 85% of asphalt is comprised of aggregate, GPR measurements are clearly impacted by mineralogical variations in the asphalt.

Aggregate, bitumen, RAP, and in some cases additional compounds, (the additional compounds are typically present in low percentages) are mixed together at the asphalt plant and the mix is delivered to the job site. It is assumed that the relative proportions of aggregate, bitumen and additional compounds remain constant, even though aggregate segregation can occur during the mixing process or during transportation of the asphalt from the mixing plant to the job site. The resulting differences in proportions of aggregate and bitumen in the segregated portion of the asphalt, will result in portions of the road being paved possessing a dielectric and calculated compaction level different than expected.

Such occurrences, while not common, are undesirable. Hence, there is a need in the art for a method to identify, and to account for, dielectric values and associated calculated compaction that do not fall within predicted limits.

SUMMARY OF THE DISCLOSED TECHNOLOGY

The disclosed technology relates to a method for determining the change in dielectric of a sample of asphalt, necessary to achieve the desired compaction level at a particular location, prior to the asphalt being rolled.

A paving machine possesses a screed, which is a large surface that presses the asphalt mix onto the road surface, such that the asphalt has an initial thickness and level of compaction. Rollers are used to further compact the applied asphalt to a desired final thickness and compaction level. The initial compaction level under the paving machine may be 75 to 85 percent, with the final desired compaction level being near 95 percent or higher. Given a well-mixed asphalt, containing aggregate with relatively uniform dielectric properties, and a flat paving surface, a consistent asphalt temperature, and a properly operated paving machine, it may be assumed that the initial compaction level of an asphalt layer laid down by the paving machine will be relatively constant across the width of screed.

The average initial compaction level is determined by the average dielectric of the asphalt compressed by the screed. Average dielectric is converted to average compaction using a predetermined relationship between dielectric and compaction, for the particular asphalt mix used as the paving material. Lateral and/or longitudinal changes in the dielectric of a segment of asphalt measured prior to roller compaction are then detected. The sources of these dielectric in-homogeneities may be found or inferred from data provided by sensors other than the GPR, on or in the vicinity of the screed and/or from other data of the road profile underneath the newly laid asphalt. If the sources of dielectric variation are found by the other sensors to be due to mix non-uniformity, or, in the absence of other sensors, are assumed to be due to mix non-uniformity, the dielectric corresponding to the desired compaction level can be adjusted at the location of the inhomogeneity. In this manner, more reliable compaction information can be used to achieve more uniformly compacted roads.

Sensors used to determine the source of dielectric in-homogeneities include, but are not limited to, pressure sensors, temperature sensors, magnetic susceptibility sensors, and LIDAR. Each sensor provides different information that may individually, or in combination with other sensors, infer the source of the dielectric inhomogeneity. For example, magnetic susceptibility sensors that measure the magnetic properties of the aggregate can relate lateral or longitudinal changes in the magnetic susceptibility of an asphalt layer to changes in aggregate mineralogy.

Pressure sensors mounted on the bottom of the screed provide information tied to the degree of compaction. A greater pressure identified by a particular sensor would infer greater compaction for a homogeneous mix at a fixed temperature. The initially more-compacted area of pavement would then require less compaction by the rollers. Temperature, as measured by a thermocouple or an infrared sensor, can be combined with information provided by a pressure sensor to infer stiffness variations in the asphalt mix. As such, the measured dielectric at the location would be in agreement with the pre-generated dielectric versus compaction relationship for the asphalt mix. The initial thickness of the asphalt layer can be obtained by measuring the difference in the elevation of the road surface prior to paving and after passage of the paving machine. Lateral and longitudinal variations in the pavement thickness may be combined with pressure sensor data to relate lower pressure areas to increased thickness and conceivably lower initial compaction and greater pressure areas to lower thickness and greater initial compaction.

Consistent pressure and temperature readings, combined with a consistent pavement thickness in the area immediately behind the paver, infer a uniformly compacted pavement. Hence, spatial variation in initial dielectric readings in the otherwise uniform area would be associated with variations in pavement aggregate dielectric and/or proportion. The measured dielectric after rolling that corresponds to the desired compaction level could then be assigned to the dielectrically in-homogeneous area by adjusting the relationship between dielectric and compaction at the location of each dielectric anomaly.

In another embodiment of the invention, the combined sensors' data and initial thickness information are used to generate a spatial map of initial compaction and the desired compaction over this area is achieved by compacting the area a predetermined amount measured by a change in pavement thickness, which, of course, may vary spatially over the area being paved. The details of combining sensor data to produce the spatial map of initial compaction may be, for example, derived from experimental test data obtained for a particular asphalt mix paved in a test area. In this embodiment, the final thickness of the asphalt may be calculated, for example, from GPR using the measured dielectric at the asphalt surface and the arrival time of the reflection from the interface between the newly laid asphalt bottom and the underlying material.

In accordance with an embodiment of the disclosed technology, there is provided a system for determining the change in dielectric or thickness of a pre-rolled asphalt layer necessary to achieve optimal compaction during rolling of the asphalt layer. The system includes a sensor arrangement including at least one sensor, selected from the group consisting of a pressure sensor, a temperature sensor, a GPR antenna, a LIDAR sensor, and a magnetic susceptibility meter. The sensor arrangement is disposed on a mobile device, and is adapted, during motion of the mobile device, to sense characteristics of asphalt pavement over which the mobile device is moving, prior to or during compaction of the asphalt pavement. The system further includes a processor, functionally associated with the sensor(s) in the sensor arrangement, and a non-transitory computer readable storage medium for instructions execution by the processor. The non-transitory computer readable storage medium has stored instructions to receive, from the sensor(s), signals relating to characteristics of the asphalt pavement over which the mobile device is moving, instructions to compute, based on the received signals, at least one compaction characteristic of the asphalt pavement, and instructions to provide a mapping of the computed compaction characteristics to regions of the asphalt pavement.

In some embodiments, the mobile device is, or includes, a paving machine, and the instructions to compute include instructions to compute an initial compaction characteristic of the asphalt pavement, following placement of the asphalt pavement and prior to rolling of the asphalt pavement.

In some embodiments, the mobile device includes a roller adapted to roll and further compact the asphalt pavement, and the instructions to compute include instructions to compute an updated compaction characteristic of the asphalt pavement, following rolling thereof.

In some other embodiments, the mobile device is independent of a machine compacting or rolling the asphalt pavement.

In some embodiments, the instructions to compute include instructions to compute an initial percent compaction of the asphalt pavement based on at least one of pressure signals received from the pressure sensors; dielectric measurements of the asphalt pavement obtained based on measurements from the GPR antenna; and a combination of pressure signals received from the pressure sensors, temperature data received from the temperature sensor, and asphalt pavement thickness data computed from signals received from the LIDAR sensor.

In some embodiments, the storage medium further has stored instructions to calculate, based on the initial percent compaction and on a desired percent compaction, a desired change in compaction of the asphalt pavement.

In some embodiments, the storage medium further has stored instructions to enhance the calculated initial percent compaction, based on at least one signal received from at least one sensor of the sensor arrangement, wherein signals from the at least one sensor were not used to compute the initial percent compaction.

In some embodiments, the instructions to compute include instructions to compute a dielectric of the asphalt pavement based on measurements from the GPR antenna, the dielectric of the asphalt pavement being correlated, by a pre-determined equation, to a compaction level of the asphalt pavement.

In some embodiments, the non-transitory computer readable storage medium further has stored instructions to compare the computed dielectric of the asphalt pavement to a desired dielectric of the asphalt pavement, and instructions, to be carried out upon identification of a discrepancy between the computed dielectric and the desired dielectric in a region of the asphalt pavement, to indicate that further compacting of the asphalt pavement in the region of the asphalt pavement may be required.

In some embodiments, the instructions to compute include instructions to compute a thickness of the asphalt pavement based on a surface dielectric measurement and a travel-time of reflection value, both received from the GPR antenna.

In accordance with an embodiment of the disclosed technology, there is provided a method for computing a compaction characteristic of asphalt pavement, the method including, during placement of the asphalt pavement, moving at least one sensor mounted onto a mobile device over a paving area, so as to obtain signals from the at least one sensor for the paving area, the at least one sensor being selected from the group consisting of a pressure sensor, a temperature sensor, a GPR antenna, a LIDAR sensor, and a magnetic sensor. Based on the obtained signals, at least one compaction characteristic of the asphalt pavement is computed. Finally, an output mapping the computed compaction characteristics to regions of the asphalt pavement is provided.

In some embodiments, the mobile device includes a paving machine applying the asphalt pavement, and the computing includes computing an initial compaction characteristic of the asphalt pavement, following placement of the asphalt pavement and prior to rolling of the asphalt pavement.

In some other embodiments, the mobile device includes a roller rolling compacting the asphalt pavement following placement thereof, and the computing includes computing an updated compaction characteristic of the asphalt pavement, following rolling thereof.

In yet other embodiments, the computing includes computing an initial percent compaction of the asphalt pavement based on at least one of pressure signals received from the pressure sensors, dielectric measurements of the asphalt pavement obtained based on measurements from the GPR antenna, and a combination of pressure signals received from the pressure sensors, temperature data received from the temperature sensor, and asphalt pavement thickness data computed from signals received from the LIDAR sensor, and the output mapping maps regions of the asphalt pavement to initial percent compaction thereof.

In some embodiments, the method further includes, following the computing, calculating, based on the initial percent compaction and on a desired percent compaction, a desired change in compaction of the asphalt pavement, and mapping the desired change in compaction to the regions of the asphalt pavement.

In some embodiments, the method further includes enhancing the computed initial percent compaction, based on at least one signal received from at least one sensor of the sensor arrangement, which was not used in the computing of the initial percent compaction.

In some embodiments, the computing includes computing a dielectric of the asphalt pavement based on measurements from the GPR antenna, the dielectric of the asphalt pavement being correlated, by a pre-determined equation, to a compaction level of the asphalt pavement.

In some embodiments, the method further includes comparing the computed dielectric of the asphalt pavement to a desired dielectric of the asphalt pavement, and upon identification of a discrepancy between the computed dielectric and the desired dielectric in a region of the asphalt pavement, further compacting the asphalt pavement in the region of the asphalt pavement.

In some embodiments, computing the at least one compaction characteristic includes comparing a computed thickness of the asphalt pavement to a desired thickness of the asphalt pavement, and upon identification of a discrepancy between the computed thickness and the desired thickness in a region of the asphalt pavement, further compacting the asphalt pavement in the region of the asphalt pavement.

In some such embodiments, the thickness of asphalt pavement is computed based on a surface dielectric measurement and a travel-time of reflection value, at least one of which is received from the GPR antenna.

DETAILED DESCRIPTION OF EMBODIMENTS OF THE DISCLOSED TECHNOLOGY

A system with at least one sensor, selected from the group consisting of a pressure sensor, a temperature sensor, at least one GPR antenna, a LIDAR sensor, and a magnetic susceptibility meter is disclosed. At least one sensor is mounted on a mobile device, and is adapted, during motion of the mobile device, to sense characteristics of asphalt pavement on which the mobile device is moving, during compaction of the asphalt pavement. A processor is functionally associated with at least one sensor. The processor receives, from the at least one sensor, signals relating to characteristics of the asphalt pavement on which the mobile device is moving, computes, based on the received signals, at least one compaction characteristic of the asphalt pavement, and provides a mapping of the computed compaction characteristics to regions of the asphalt pavement.

Embodiments of the disclosed technology will become clearer in view of the following description of the drawings.

Figure 1A:
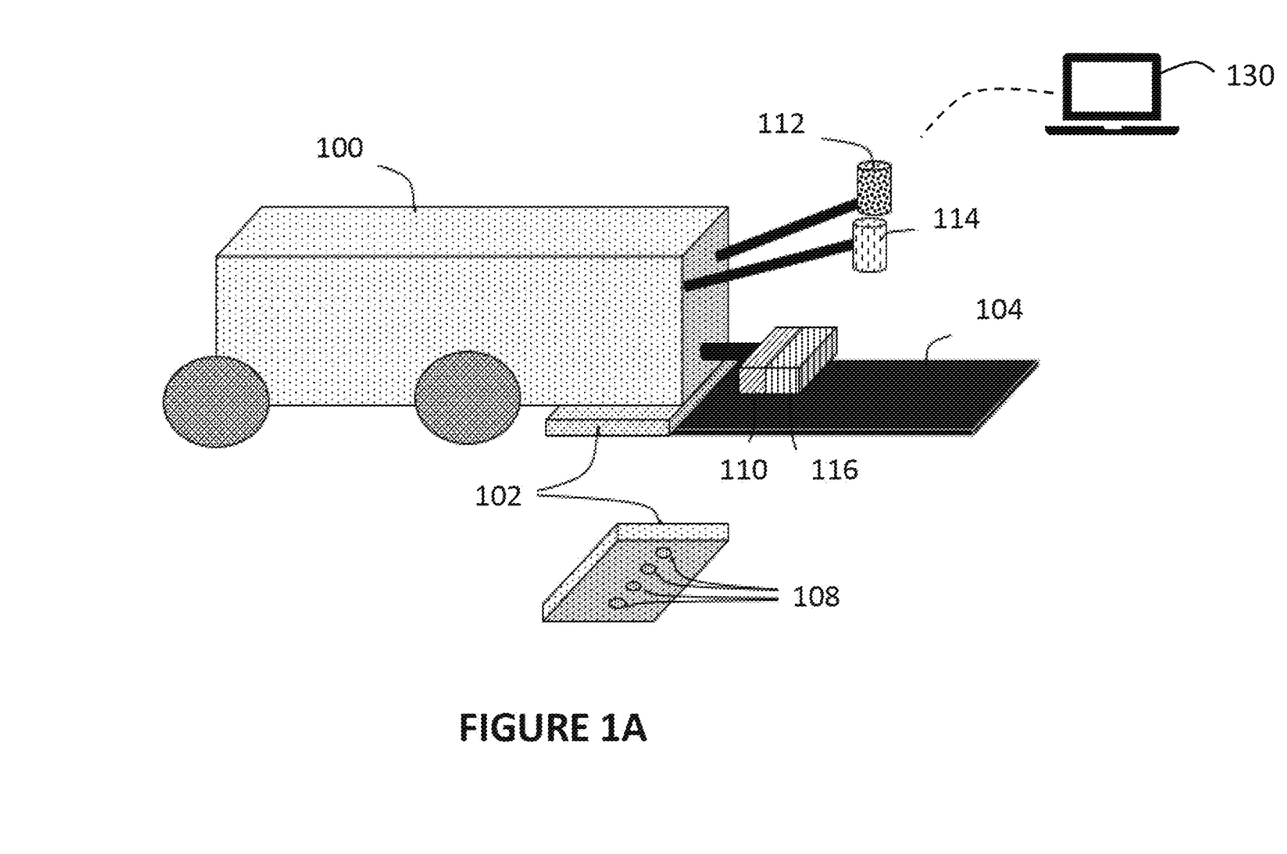
FIGS. 1A and 1B are schematic illustrations of embodiments of compaction level measuring machines, for measuring a compaction level of an asphalt layer, according to embodiments of the disclosed technology.
Figure 1B:
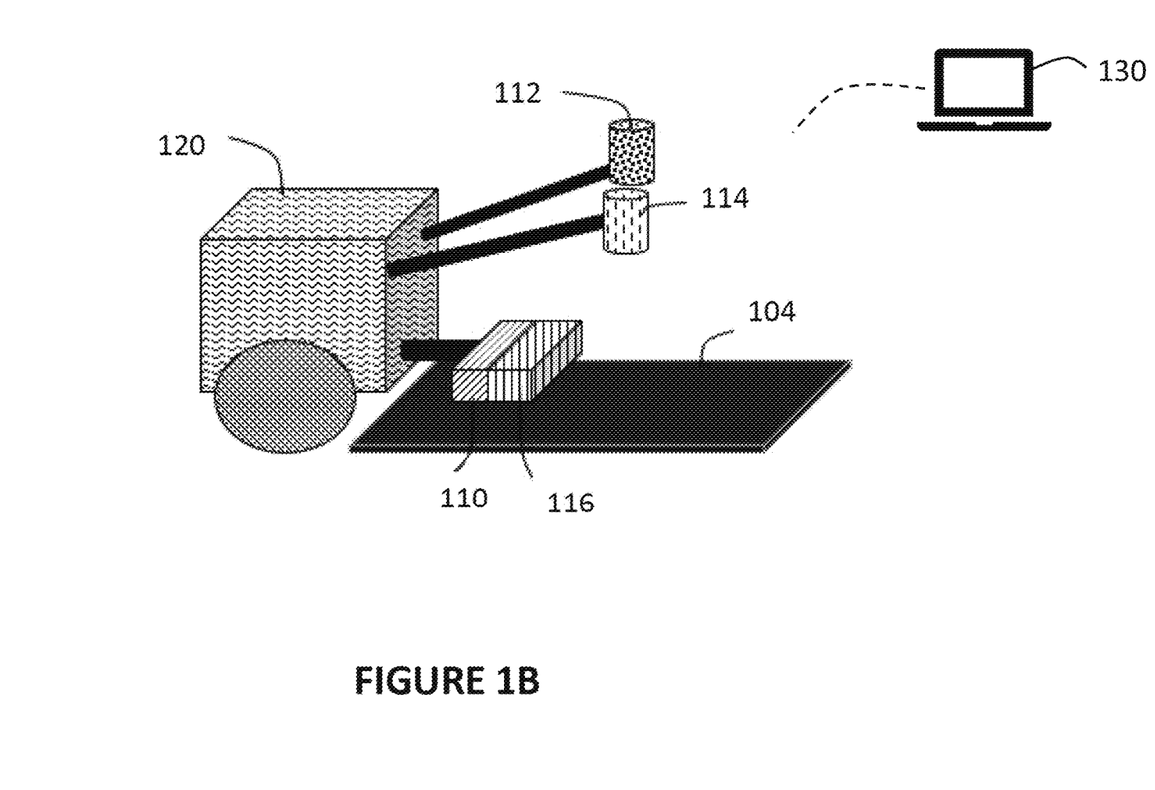

Reference is now made to FIGS. 1A and 1B, which are schematic illustrations of embodiments of compaction level measuring machines, for measuring a compaction level of an asphalt layer, according to embodiments of the disclosed technology.

In FIG. 1A, a paving machine 100 includes a screed plate 102 adapted to apply compressing pressure to an asphalt layer 104 being paved, which results in an initial compaction level. A plurality of pressure sensors 108 are mounted onto a pavement facing surface of screed plate 102, to sense, or identify, the pressure applied to asphalt layer 104 as paving machine 100 lays down the asphalt layer.

Additional sensors may be mounted onto paving machine 100, for example above, or behind, screed 102, such that the sensors are adapted to provide signals relating to asphalt being compressed by the screed 102. The additional sensors may include one or more of GPR antennas 110, a temperature sensor 112, a Light Detection and Ranging (LIDAR) sensor 114, and one or more magnetic susceptibility meters 116.

Turning to FIG. 1B, in some embodiments, rather than being mounted directly on the paving machine, the GPR antennas 110, the temperature sensor 112, the Light Detection and Ranging (LIDAR) sensor 114, and the one or more magnetic susceptibility meters 116 may be mounted onto a mobile platform 120, separate from a paving machine (not explicitly shown in FIG. 1B). In such embodiments, the mobile platform 120 is adapted to travel behind the paving machine, such that the sensor(s) thereof can read/provide signals relating to the asphalt layer 104 compressed by the screed of the paving machine.

Figure 2A:
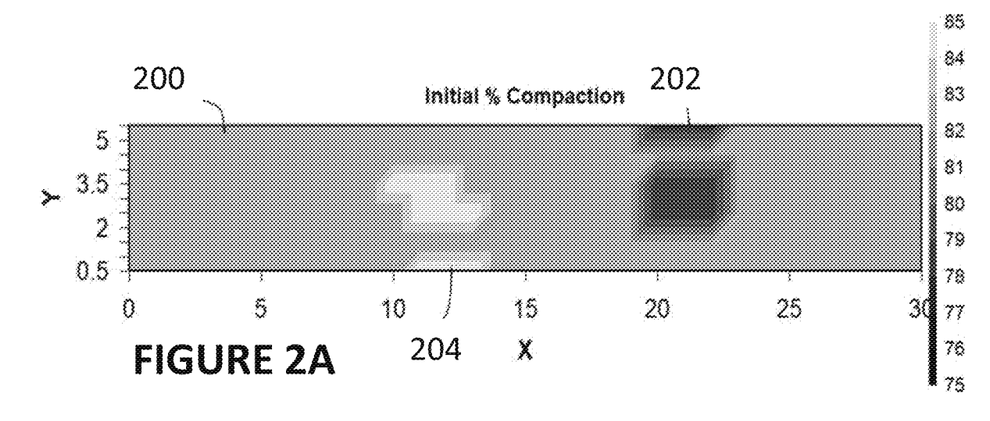
FIG. 2A is a map of an initial percent compaction, the map being generated from sensor data after the paving machine has laid down the asphalt, and prior to rolling of the new asphalt layer.

In use, different combinations of the sensors, 108, 110, 112, 114, and/or 116, are adapted to provide signals so as to enable a control unit to generate an initial compaction distribution map, as illustrated in FIG. 2A. In some embodiments, the processor 130 may be an on-board processor, forming part of the paving machine 100 or of the mobile platform 120. In other embodiments, the processor 130 may be a remote processor, to which signals obtained by the sensor(s) are transmitted, for example by wireless communication, from the sensors or from another computing device having networked communication with processor 130. Specific uses of the sensors mounted onto paving machine 100 and/or mobile platform 120 are described hereinbelow with respect to FIGS. 2A to 6.

Figure 2B:
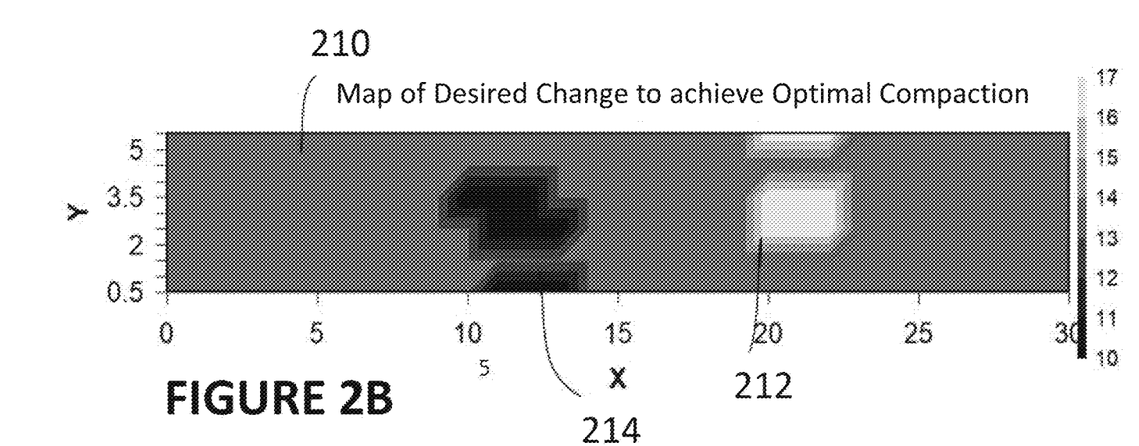
FIG. 2B is a map of the desired change in a measurable quantity, such as dielectric or thickness to achieve a final desired percent compaction.

Reference is now made to FIGS. 2A and 2B, which are, respectively, an initial percent compaction map, and a map of desired change in measurable quantity to achieve optimal compaction, both representing the same paved area.

FIG. 2A shows a map 200 of an initial percent compaction, the map being generated from sensor data collected after a paving machine has laid down the asphalt layer, and prior to rolling of the paved asphalt, for example by sensors 108, and/or by sensors 110, 112, 114, and/or 116 of FIGS. 1A and 1B. The map relates to a spatial distribution of the percent compaction of a paved area. However, the map may relate to any other suitable metric indicative of the level of compaction of the area, such as density or percent void content. As seen in FIG. 2A, the generated map 200 demonstrates variability in the compaction levels within the map. For example, in the region indicated by reference numeral 202 the percent compaction is approximately 79%, lower than in most of the area included in map 200 where the percent of compaction is approximately 82%. As another example, in the region indicated by reference numeral 204, the percent compaction is approximately 85%, greater than the approximate 82% compaction in most of the area included in map 200.

Given a pre-determined desired final percent of compaction, and using map 200 of the initial compaction level, a second map 210, illustrated in FIG. 2B, may be generated. The second map 210 is indicative of a change in a measurable quantity, required to achieve the desired level of compaction or compaction characteristics for the area. This measurable quantity may be in units of dielectric property/ value or pavement layer thickness. Given the desire that the whole area have the same compaction level, regions of the area which have a lower initial compaction level would require a greater change in compaction (a greater amount of additional compaction) or compaction characteristics and regions of the area which have a higher initial compaction level would require a lesser change in compaction or compaction characteristics (a smaller amount of additional compaction). For example, in region 212 of map 210, which corresponds to region 202 of map 200 having a lower initial compaction level, additional compaction measured by a dielectric value change or asphalt pavement thickness change is required to reach the desired compaction level or compaction characteristics, relative to the compaction required in most of the area included in map 210. As another example, in region 214 of map 210, which corresponds to region 204 of map 200 having a higher initial compaction level, less compaction is required than in most of the area included in map 210.

Figure 3A:
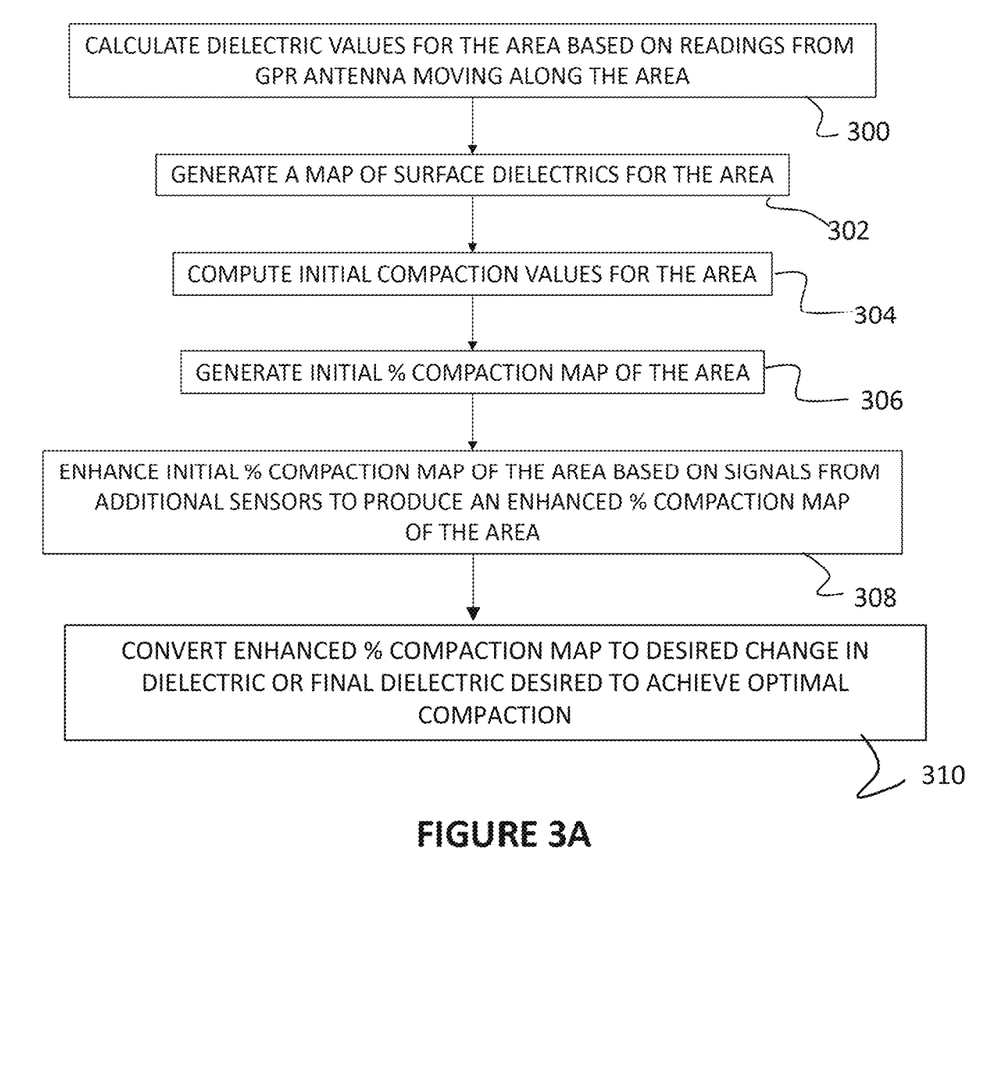
FIGS. 3A and 3B are flow charts of embodiments of methods for generating the measurable quantity for optimal compaction map of asphalt in a given region, according to embodiments of the disclosed technology.
Figure 3B:
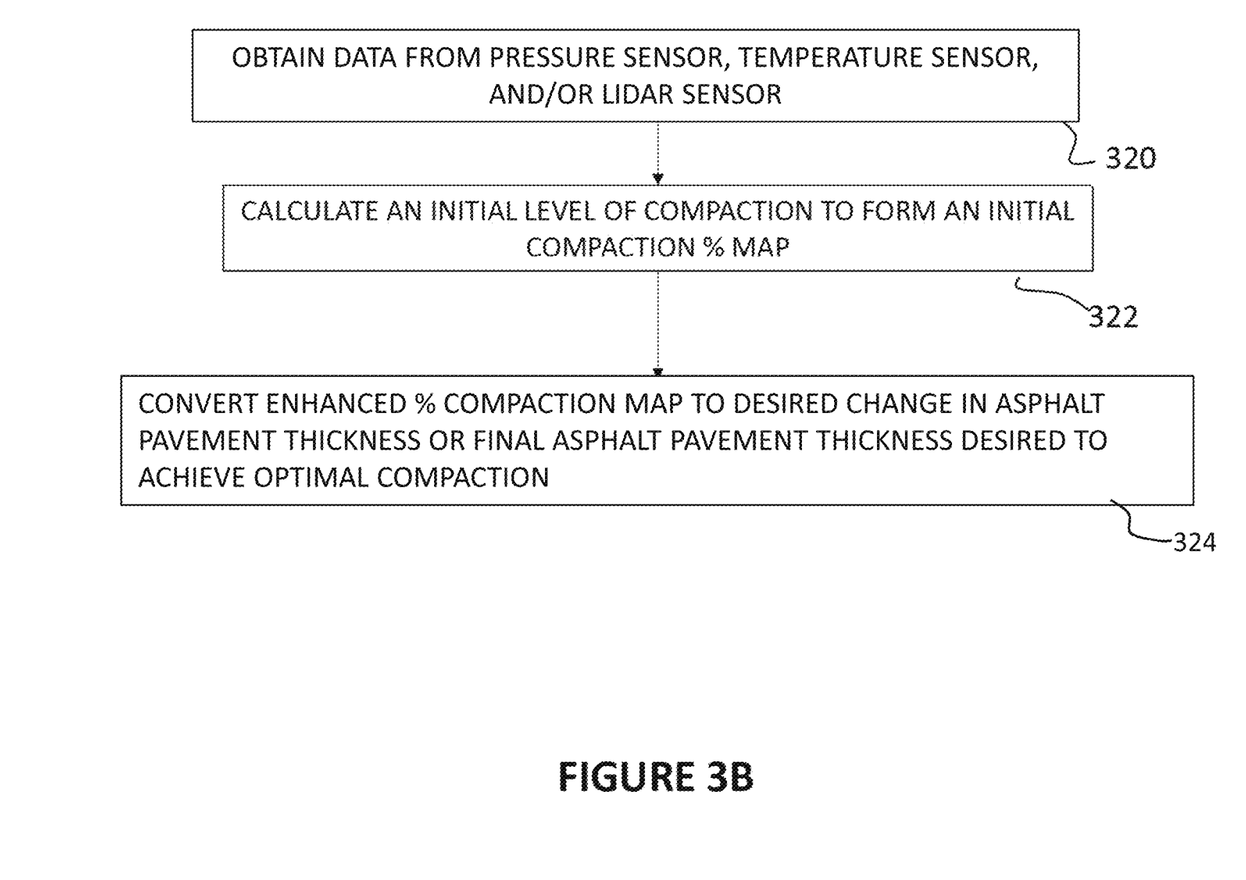

Reference is now made to FIGS. 3A and 3B, which are flow charts of embodiments of methods for obtaining change in measurable quantity to achieve optimal compaction maps of asphalt in a given area, according to embodiments of the disclosed technology, and to FIGS. 4A, 4B, 4C and 4D, which are maps reflective of different stages of the method of FIG. 3A.

Figure 4A:
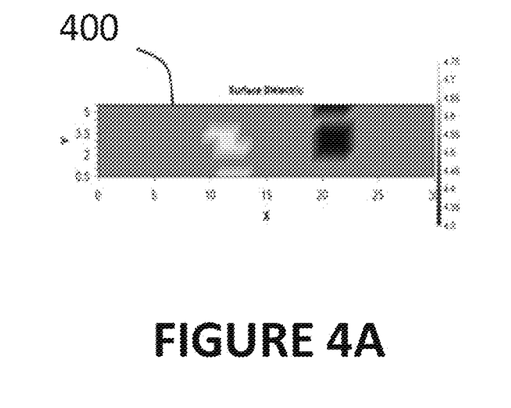
FIGS. 4A, 4B, 4C, and 4D are maps reflective of different stages of the method of FIG. 3A.

As seen in FIG. 3A, at step 300 readings from GPR antennas moving along the area, such as antennas 110 of FIGS. 1A and 1B, are used to calculate dielectric values for the area, and a map of the surface dielectric, such as map 400 illustrated in FIG. 4A, is generated at step 302.

Figure 4B:
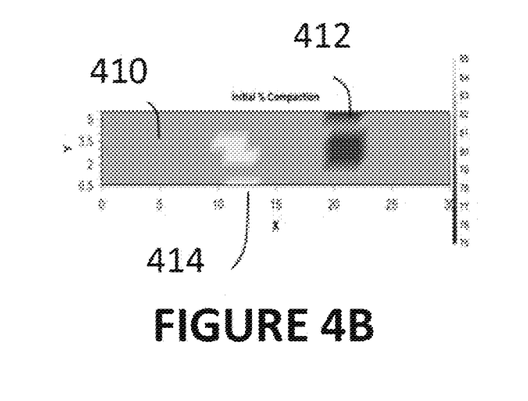

At step 304, initial compaction values of the area are then generated by applying the measured dielectric to a pre-generated calibration curve equation, which relates dielectrics to compaction for a particular asphalt mix. Subsequently, the initial compaction values are used to generate an initial % compaction map, such as map 410 illustrated in FIG. 4B, at step 306. However, it is appreciated that the equation used in step 304 may relate the dielectric values to another metric representing compaction levels, and the map generated at step 306 may be an initial compaction map based on another metric, such as density or percent void content. As seen in FIG. 4B, map 410 includes % compaction anomalies at regions 412 and 414.

Figure 4C:
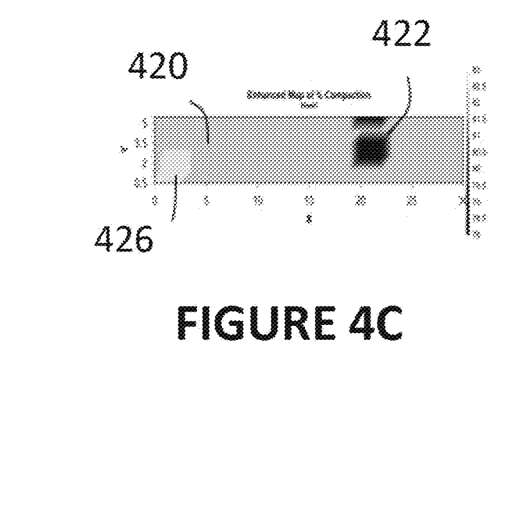

At step 308, the initial % compaction map generated at step 306 may optionally be enhanced based on signals received from additional sensors, such as sensors 112, 114, and/or 116 of FIGS. 1A and 1B, to produce an enhanced % compaction map, such as map 420 illustrated in FIG. 4C. Typically, the enhancement corrects for dielectric values not directly related to compaction differences for the particular mix. The enhanced % compaction map may be used to determine where, and how much, additional compaction is required, as described with respect to FIGS. 2B, 5, and 6. At a final step 310, the enhanced % compaction map is converted back to the desired change in dielectric or final dielectric desired to achieve optimal compaction during the rolling process.

Figure 4D:
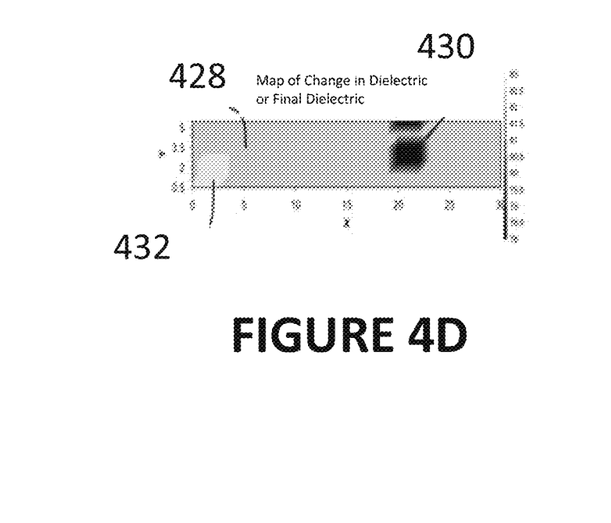

As seen in FIG. 4C, while the enhanced initial % compaction map still shows regions 422 and 426 with % compaction anomalies, these regions do not necessarily correlate to the regions demonstrating anomalies in the initial % compaction map, prior to enhancement thereof. Specifically, in the illustrated embodiment, region 422 having anomalous compaction in enhanced map 420 corresponds to region 412 having anomalous compaction in initial map 410. However, region 426 having anomalous compaction in enhanced map 420 does not correspond to an anomalous region in initial map 410, and the anomaly in region 414 of map 410 seems to have been "fixed" in the corresponding area of map 420. This apparent inconsistency may be the result of the reason for the anomalous calculation. For example, a magnetic susceptibility variation may lead to an adjustment of the calculated initial compaction in certain areas because it is indicative of different aggregate than used to generate the compaction versus dielectric calibration curve equation used at step 304. In this example, the anomaly is not really a compaction anomaly, but rather an aggregate anomaly, and the correlation of dielectric to % compaction, for that aggregate in that region, was incorrectly used in generating the initial compaction map 410, and use of additional sensors indicated that the region was indeed at the normal compaction level based on an equation suitable for the actual aggregate in that region. FIG. 4D illustrates the last step in the process, which is to convert the enhanced compaction map values to a map 428 of desired change in dielectric or final dielectric following rolling, to achieve optimal compaction. The locations where there are compaction differences 422, 426 in the map of FIG. 4C, often correspond to desired dielectric differences 430, 432.

FIG. 3B shows another embodiment for creating a desired change in measurable quantity map, to be used when further rolling the paved area. As seen in FIG. 3B, in an initial step 320, data may optionally be obtained from a pressure sensor, such as sensors 108 of FIG. 1A as well as from a temperature sensor, such as sensor 112 of FIGS. 1A and 1B. Additionally, initial thickness data obtained from a LIDAR sensor, such as sensor 114 of FIGS. 1A and 1B. The obtained data is combined, at step 322, to calculate an initial level of compaction distribution and to form an initial % compaction map. Typically, a pre-established empirical relationship between the three data types is used to convert the data into information relating to % compaction. The initial compaction map is then converted into the desired change in asphalt pavement thickness or the desired final asphalt pavement thickness necessary to achieve optimal compaction at step 324.

Figure 5:
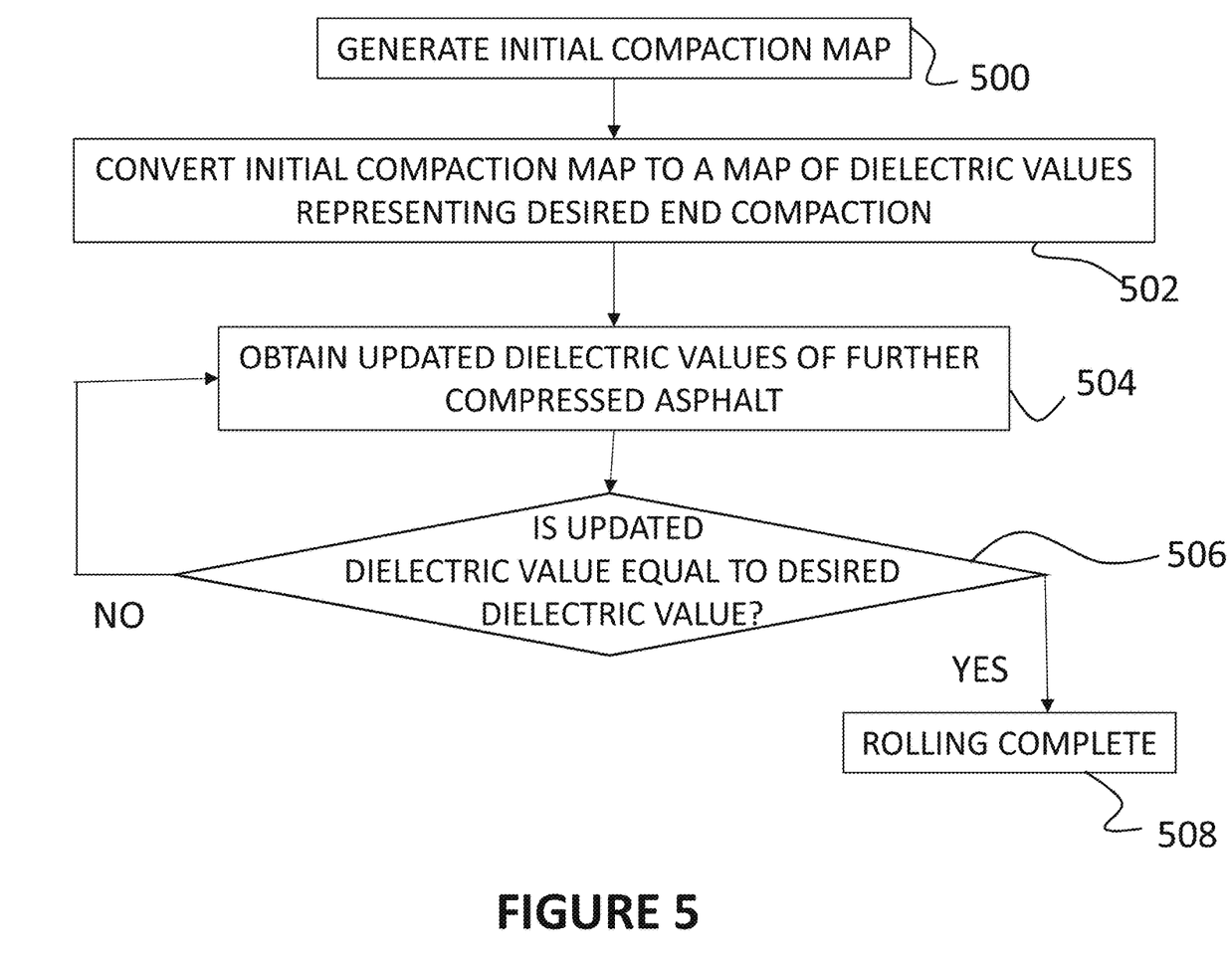
FIG. 5 is a flow chart of a method for obtaining a desired final dielectric from initial compaction values, so as to obtain a desired compaction level, according to an embodiment of the disclosed technology.

Reference is now made to FIG. 5, which is a flow chart of a method for obtaining a desired final dielectric from initial compaction values, so as to obtain a desired compaction level, according to an embodiment of the disclosed technology.

The change in compaction as the asphalt is being rolled may be assessed using a GPR antenna or other sensor mounted onto the roller, or a separate mobile platform moving among the rollers, for example as illustrated in FIG. 1B.

As seen in FIG. 5, an initial compaction map is generated at step 500, for example using the method of FIG. 3A or of FIG. 3B. At step 502, the initial compaction map is then converted to a map of dielectric values, representing desired end compaction, for example using a pre-generated calibration curve equation, which relates dielectrics to compaction for a particular asphalt mix, as discussed hereinabove.

During (or after) passage of the roller over the paved area, updated dielectric values of the now further compressed asphalt are obtained by the GPR antenna, at step 504. At step 506, the updated dielectric values for each region of the map are compared to the values in the map of desired end compaction dielectric values. If the updated dielectric values match the desired values, the rolling is complete, as indicated at reference numeral 508. Otherwise, if the updated dielectric values do not match the desired values, the flow returns to step 504, for another passage of the roller over the paved area and updating of the dielectric measurements.

Figure 6:
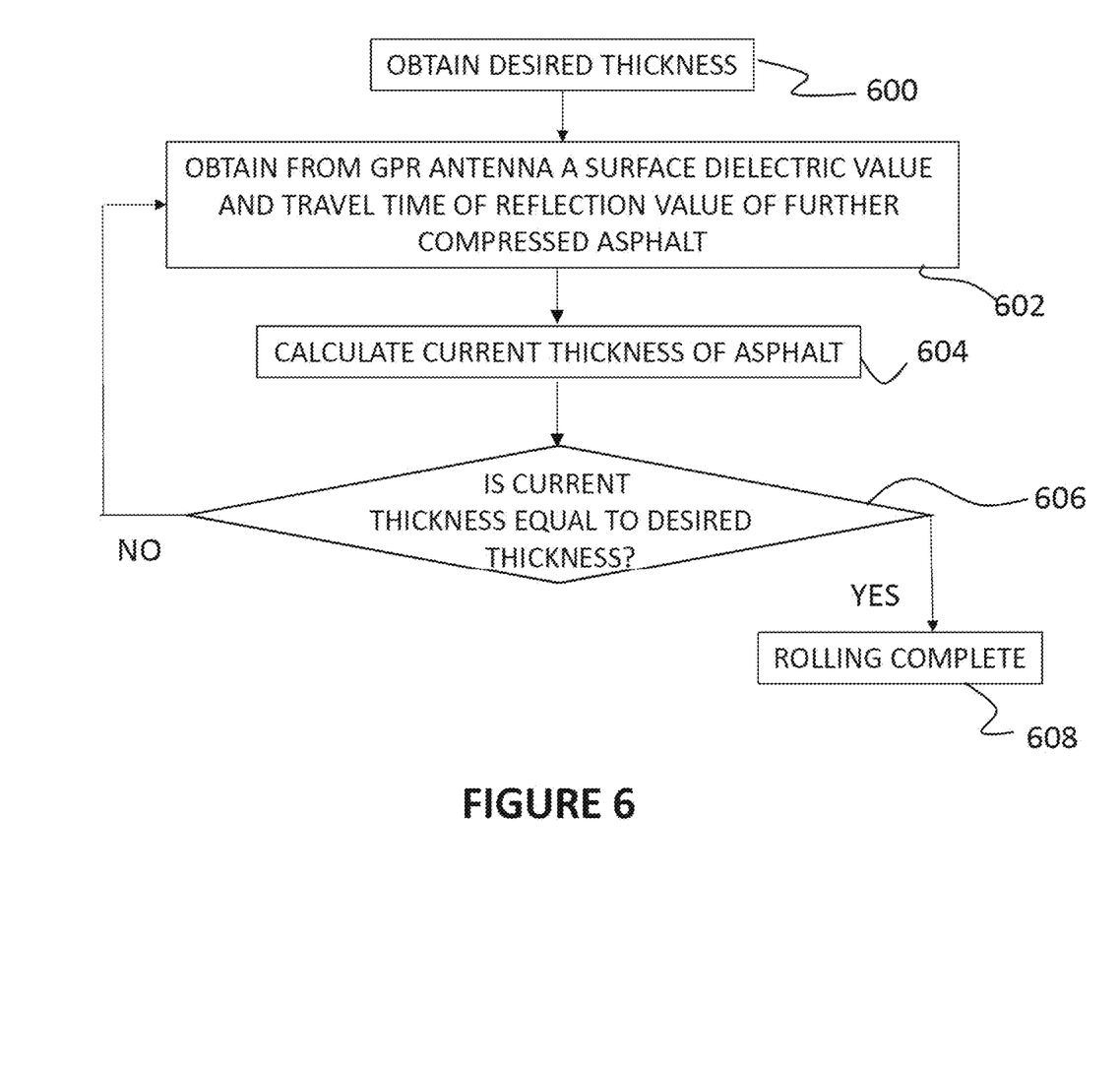
FIG. 6 is a flow chart of a method for obtaining a desired final thickness from initial compaction values, so as to obtain a desired compaction level, according to an embodiment of the disclosed technology.

Reference is now made to FIG. 6, which is a flow chart of a method for obtaining a desired final thickness from initial compaction values, so as to obtain a desired compaction level, according to an embodiment of the disclosed technology.

As seen in FIG. 6, the desired thickness of the asphalt, at the end of the compaction process, which may be calculated or pre-determined, is obtained at step 600. At step 602, during (or after) passage of the roller over the paved area, surface dielectric values and travel-time of reflection (from a bottom surface of the asphalt) values are obtained by a GPR antenna, for example an antenna mounted onto the roller or forming part of a mobile unit, such as unit 120 of FIG. 1B. The obtained values are used, at step 604, to calculate a current thickness of the asphalt, using an equation which relates the pavement thickness from the surface dielectric and measured travel time as known in the art.

For each region of the map, the calculated thickness is compared to the desired thickness at step 606. If the calculated thickness matches the desired thickness, the rolling is complete, as indicated at reference numeral 608. Otherwise, if the calculated thickness does not match the desired thickness, the flow returns to step 602, for another passage of the roller over the paved area and updating of the measurements obtained from the GPR antenna.

For purposes of this disclosure, the term "substantially" is defined as "at least 95% of" the term which it modifies.

For purposes of this disclosure, the term "optimal" is defined as having the best value of a certain characteristic. In the context of the disclosure, with respect to compaction of asphalt pavement, optimal compaction or compaction characteristic is typically achieved when at least one characteristic of the asphalt pavement is uniform, such as uniform dielectric, uniform thickness, and the like.

For purposes of this disclosure, the phrase "A or B" relates to an inclusive or operator, and includes the options "only A", "only B", as well as "A and B".

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A system for determining the change in dielectric property/value or thickness of a pre-rolled asphalt layer necessary to achieve optimal compaction during rolling of the asphalt layer, the system comprising:
   a sensor arrangement including sensors, selected from the group consisting of a pressure sensor, a temperature sensor, a Ground Penetrating Radar antenna, a LIDAR/Light Detection and Ranging sensor, and a magnetic susceptibility meter, said sensor arrangement being disposed on a mobile device, and being adapted, during motion of said mobile device, to sense characteristics of asphalt pavement over which said mobile device is moving, prior to or during compaction of said asphalt pavement;
   a processor, functionally associated with said sensors in said sensor arrangement; and
   a non-transitory computer readable storage medium for instructions execution by the processor, said non-transitory computer readable storage medium having stored:
      instructions to receive, from said sensors, signals relating to characteristics of said asphalt pavement over which said mobile device is moving;
      instructions to compute, based on said received signals, at least one compaction characteristic of said asphalt pavement; and instructions to provide a mapping of said computed compaction characteristics to regions of said asphalt pavement.

2. The system of claim 1, wherein said mobile device comprises a paving machine, and said instructions to compute include instructions to compute an initial compaction characteristic of said asphalt pavement, following placement of said asphalt pavement and prior to rolling of said asphalt pavement.

3. The system of claim 1, wherein said mobile device comprises a roller adapted to roll and further compact said asphalt pavement, and said instructions to compute include instructions to compute an updated compaction characteristic of said asphalt pavement, following rolling thereof.

4. The system of claim 1, wherein said mobile device is independent of a machine compacting or rolling said asphalt pavement.

5. The system of claim 1, wherein said instructions to compute comprise instructions to compute an initial percent compaction of said asphalt pavement based on:
 pressure signals received from said pressure sensors;
 dielectric measurements of said asphalt pavement obtained based on measurements from said Ground Penetrating Radar antenna; or
 a combination of pressure signals received from said pressure sensors, temperature data received from said temperature sensors, and asphalt pavement thickness data computed from signals received from said LIDAR sensors.

6. The system of claim 5, wherein said storage medium further has stored instructions to calculate, based on said initial percent compaction and on a desired percent compaction, a desired change in compaction of said asphalt pavement.

7. The system of claim 5, wherein said storage medium further has stored instructions to enhance said calculated initial percent compaction, based on signals received from said sensors of said sensor arrangement, wherein a signal from at least one said sensor was not used to compute said initial percent compaction.

8. The system of claim 1, wherein said instructions to compute comprise instructions to compute the dielectric property/value of said asphalt pavement based on measurements from said Ground Penetrating Radar antenna, said dielectric property/value of said asphalt pavement being correlated, by a pre-determined equation, to a compaction level of said asphalt pavement.

9. The system of claim 8, wherein said non-transitory computer readable storage medium further has stored:
 instructions to compare said computed dielectric property/value of said asphalt pavement to a desired dielectric property/value of said asphalt pavement; and
 instructions, to be carried out upon identification of a discrepancy between said computed dielectric property/value and said desired dielectric property/value in a region of said asphalt pavement, to indicate that further compacting of said asphalt pavement in said region of said asphalt pavement may be required.

10. The system of claim 1, wherein said instructions to compute comprise instructions to compute a thickness of said asphalt pavement based on a surface dielectric measurement and a travel-time of reflection value, both received from said Ground Penetrating Radar antenna.

11. A method for computing a compaction characteristic of asphalt pavement, the method comprising:
 during placement of said asphalt pavement, moving sensors mounted onto a mobile device over a paving area, so as to obtain signals from said sensors for said paving area, said sensors being selected from the group consisting of pressure sensors, temperature sensors, a Ground Penetrating Radar antenna, LIDAR/Light Detection and Ranging sensors, and magnetic sensors;
 computing, based on said obtained signals, at least one compaction characteristic of said asphalt pavement;
 providing an output mapping said computed compaction characteristic to regions of said asphalt pavement;
 wherein said computing comprises computing an initial percent compaction of said asphalt pavement based on at least one of:
 pressure signals received from said pressure sensors;
 dielectric property/value measurements of said asphalt pavement obtained based on measurements from said Ground Penetrating Radar antenna; and
 a combination of pressure signals received from said pressure sensors, temperature data received from said temperature sensors, and asphalt pavement thickness data computed from signals received from said LIDAR sensors.

12. The method of claim 11, further comprising, following said computing, calculating, based on said initial percent compaction and on a desired percent compaction, a desired change in compaction of said asphalt pavement, and mapping said desired change in compaction to said regions of said asphalt pavement.

13. The method of claim 11, further comprising enhancing said computed initial percent compaction, based on at least one signal received from at least one said sensor of said sensor arrangement, which was not used in said computing of said initial percent compaction.

14. The method of claim 11, wherein said computing said at least one compaction characteristic comprises:
 comparing a computed thickness of said asphalt pavement to a desired thickness of said asphalt pavement; and
 upon identification of a discrepancy between said computed thickness and said desired thickness in a region of said asphalt pavement, further compacting said asphalt pavement in said region of said asphalt pavement;
 wherein said thickness of asphalt pavement is computed based on a surface dielectric property/value measurement and a travel-time of reflection value, at least one of which is received from said Ground Penetrating Radar antenna.

15. A method for computing a compaction characteristic of asphalt pavement, the method comprising:
 during placement of said asphalt pavement, moving sensors mounted onto a mobile device over a paving area, so as to obtain signals from said sensors for said paving area, said sensors being selected from the group consisting of pressure sensors, temperature sensors, a Ground Penetrating Radar antenna, LIDAR/Light Detection and Ranging sensors, and magnetic sensors;
 computing, based on said obtained signals, at least one compaction characteristic of said asphalt pavement; and
 providing an output mapping said computed compaction characteristics to regions of said asphalt pavement;
 wherein said computing comprises computing a dielectric property/value of said asphalt pavement based on measurements from said Ground Penetrating Radar antenna, said property/value of said asphalt pavement being correlated, by a pre-determined equation, to a compaction level of said asphalt pavement.

16. The method of claim 15, further comprising:
comparing said computed dielectric property/value of said asphalt pavement to a desired dielectric property/value of said asphalt pavement; and
upon identification of a discrepancy between said computed property/value and said desired dielectric property/value in a region of said asphalt pavement, further compacting said asphalt pavement in said region of said asphalt pavement.

* * * * *